United States Patent [19]

Cross, III et al.

[11] Patent Number: 6,012,919
[45] Date of Patent: *Jan. 11, 2000

[54] TRIPLE COMPOSITE PERFORMANCE ENHANCING DENTAL APPLIANCE

[76] Inventors: Henry D. Cross, III, 546 Old Field Rd., Murrell's Inlet, S.C. 29576; Paul C. Belvedere, 5824 Creek Valley Rd., Edina, Minn. 55439; Jon D. Kittelsen, 1511 Innsbruck Dr. North, Fridley, Minn. 55432

[ * ] Notice: This patent is subject to a terminal disclaimer.

[21] Appl. No.: 09/241,181

[22] Filed: Feb. 1, 1999

Related U.S. Application Data

[63] Continuation of application No. 09/022,319, Feb. 11, 1998, Pat. No. 5,865,619, which is a continuation-in-part of application No. 08/764,900, Dec. 16, 1996, Pat. No. 5,718,575, which is a continuation-in-part of application No. 08/375,921, Jan. 19, 1995, Pat. No. 5,584,687, which is a continuation of application No. 08/104,489, Aug. 9, 1993, abandoned.

[51] Int. Cl.[7] ...................................................... A61C 3/00
[52] U.S. Cl. ................................................. 433/6; 128/861
[58] Field of Search ................................ 433/6; 128/858, 128/859, 860, 861, 862

[56] References Cited

U.S. PATENT DOCUMENTS

| | | |
|---|---|---|
| 257,038 | 4/1882 | McMann . |
| D. 328,494 | 8/1992 | Schwendeman . |
| D. 343,928 | 2/1994 | Kittelsen . |
| D. 356,188 | 3/1995 | Kittelsen . |
| D. 373,421 | 9/1996 | Brown . |
| D. 397,442 | 8/1998 | Kittelsen . |
| 1,117,928 | 11/1914 | Thurmond . |
| 1,323,832 | 12/1919 | Chige . |
| 1,461,209 | 7/1923 | Bridges . |
| 1,470,888 | 10/1923 | Smedley . |
| 1,487,392 | 3/1924 | Lee . |
| 2,118,980 | 5/1938 | Montgomery . |
| 2,257,709 | 9/1941 | Anderson . |
| 2,423,005 | 6/1947 | Chaiken . |
| 2,630,117 | 3/1953 | Coleman . |
| 2,643,652 | 6/1953 | Cathcart . |

(List continued on next page.)

FOREIGN PATENT DOCUMENTS

| | | |
|---|---|---|
| 1147-583 | 6/1983 | Canada . |
| 480423 | 8/1929 | Germany . |

OTHER PUBLICATIONS

American Dental Association, "Mouth Protectors: Give Your Teeth A Sporting Chance".

"Muscular Strength Correlated to Jaw Posrue and the Temporomandibular Joint," Stephen D. Smith, D.M.D., NYS Dental Journal, vol. 44, No. 7, Aug.–Sep., 1978.

"Reduction of Stress in the Chewing Mechanism—Part III", William B. May, D.D.S., Basal Facts, Vol. 3, No. 1, pp. 22–28.

*Primary Examiner*—Nicholas D. Lucchesi
*Attorney, Agent, or Firm*—Gerald E. Helget; Mackall, Crounse & Moore, PLC

[57] ABSTRACT

A performance enhancing and force absorbing dental appliance adapted to lie within the mouth of an athlete consists of an occlusal posterior pad made of triple composite material with a base having a top layer of impressionable material, an intermediate layer of hard material and a somewhat impressionable bottom layer, engageable with the occlusal surfaces to space apart the upper and lower teeth, to absorb shock and clenching stress. An adjustable arch adapted to expand and contract to be molded to the palate is provided connecting the posterior pads together within the mouth and out of the way of the tongue to maintain the position of the occlusal posterior pads within the mouth during use and to prevent loss of the pads such as by swallowing. An optional expandable stiffener may be embedded in the arch. Optional protrusions extend from the bottom layer through the intermediate layer and top layer to engage the central fossae of the molar teeth.

20 Claims, 7 Drawing Sheets

U.S. PATENT DOCUMENTS

| | | |
|---|---|---|
| 2,659,366 | 11/1953 | Savarese . |
| 2,669,988 | 2/1954 | Carpenter . |
| 2,678,043 | 5/1954 | Stark . |
| 2,694,397 | 11/1954 | Herms . |
| 2,702,032 | 2/1955 | Freedland . |
| 2,708,931 | 5/1955 | Freedland . |
| 2,750,941 | 6/1956 | Cathcart . |
| 2,833,278 | 5/1958 | Ross . |
| 2,847,003 | 8/1958 | Helmer . |
| 2,933,811 | 4/1960 | Lifton . |
| 2,966,908 | 1/1961 | Cathcart . |
| 3,016,052 | 1/1962 | Zubren . |
| 3,058,462 | 10/1962 | Greenblum . |
| 3,073,300 | 1/1963 | Berghash . |
| 3,082,765 | 3/1963 | Helmer . |
| 3,107,667 | 10/1963 | Moore . |
| 3,124,129 | 3/1964 | Grossberg . |
| 3,126,002 | 3/1964 | Owens . |
| 3,203,417 | 8/1965 | Helmer . |
| 3,207,153 | 9/1965 | Goldstein . |
| 3,223,085 | 12/1965 | Gores . |
| 3,247,844 | 4/1966 | Berghash . |
| 3,312,218 | 4/1967 | Jacobs . |
| 3,319,626 | 5/1967 | Lindsay . |
| 3,407,809 | 10/1968 | Ross . |
| 3,411,501 | 11/1968 | Greenberg . |
| 3,416,527 | 12/1968 | Hoef . |
| 3,448,738 | 6/1969 | Berghash . |
| 3,457,916 | 7/1969 | Wolicki . |
| 3,485,242 | 12/1969 | Greenberg . |
| 3,496,936 | 2/1970 | Gores . |
| 3,505,995 | 4/1970 | Greenberg . |
| 3,513,838 | 5/1970 | Foderick . |
| 3,518,988 | 7/1970 | Gores . |
| 3,532,091 | 10/1970 | Lerman . |
| 3,682,164 | 8/1972 | Miller . |
| 3,692,025 | 9/1972 | Greenberg . |
| 3,768,465 | 10/1973 | Helmer . |
| 3,864,832 | 2/1975 | Carlson . |
| 3,916,527 | 11/1975 | Linkow . |
| 3,924,638 | 12/1975 | Mann . |
| 3,943,924 | 3/1976 | Kallestad . |
| 4,030,493 | 6/1977 | Walters . |
| 4,044,762 | 8/1977 | Jacobs . |
| 4,063,552 | 12/1977 | Going, Jr. . |
| 4,114,614 | 9/1978 | Kesling . |
| 4,185,817 | 1/1980 | Peterson . |
| 4,211,008 | 7/1980 | Lerman . |
| 4,330,272 | 5/1982 | Bergersen . |
| 4,337,765 | 7/1982 | Zimmerman . |
| 4,348,178 | 9/1982 | Kurz . |
| 4,376,628 | 3/1983 | Aardse . |
| 4,457,708 | 7/1984 | Dufour . |
| 4,490,112 | 12/1984 | Tanaka . |
| 4,519,386 | 5/1985 | Sullivan . |
| 4,568,280 | 2/1986 | Ahlin . |
| 4,591,341 | 5/1986 | Andrews . |
| 4,671,766 | 6/1987 | Norton . |
| 4,672,959 | 6/1987 | May . |
| 4,727,867 | 3/1988 | Knoderer . |
| 4,755,139 | 7/1988 | Abbatte . |
| 4,763,791 | 8/1988 | Halverson . |
| 4,765,324 | 8/1988 | Lake, Jr. . |
| 4,791,941 | 12/1988 | Schaefer . |
| 4,793,803 | 12/1988 | Martz . |
| 4,799,500 | 1/1989 | Newbury . |
| 4,810,192 | 3/1989 | Williams . |
| 4,848,365 | 7/1989 | Guarlotti . |
| 4,867,147 | 9/1989 | Davis . |
| 4,976,618 | 12/1990 | Anderson . |
| 4,977,905 | 12/1990 | Kittelsen . |
| 5,031,611 | 7/1991 | Moles . |
| 5,031,638 | 7/1991 | Castaldi . |
| 5,063,940 | 11/1991 | Adell . |
| 5,076,785 | 12/1991 | Tsai . |
| 5,082,007 | 1/1992 | Adell . |
| 5,112,225 | 5/1992 | Diesso . |
| 5,117,816 | 6/1992 | Shapiro . |
| 5,152,301 | 10/1992 | Kittelsen . |
| 5,154,609 | 10/1992 | George . |
| 5,165,424 | 11/1992 | Silverman . |
| 5,194,003 | 3/1993 | Garay . |
| 5,194,004 | 3/1993 | Bergersen . |
| 5,234,005 | 8/1993 | Kittelsen . |
| 5,235,991 | 8/1993 | Minneman . |
| 5,259,762 | 11/1993 | Farrell . |
| 5,277,203 | 1/1994 | Hays . |
| 5,293,880 | 3/1994 | Levitt . |
| 5,297,960 | 3/1994 | Burns . |
| 5,299,936 | 4/1994 | Ueno . |
| 5,302,117 | 4/1994 | Kraut . |
| 5,313,960 | 5/1994 | Tomasi . |
| 5,316,474 | 5/1994 | Robertson . |
| 5,320,114 | 6/1994 | Kittelsen . |
| 5,323,787 | 6/1994 | Pratt . |
| 5,336,086 | 8/1994 | Simmen . |
| 5,339,832 | 8/1994 | Kittelsen . |
| 5,353,810 | 10/1994 | Kittelsen . |
| 5,365,946 | 11/1994 | McMillan . |
| 5,385,155 | 1/1995 | Kittelsen . |
| 5,386,821 | 2/1995 | Poterack . |
| 5,401,234 | 3/1995 | Libin . |
| 5,447,168 | 9/1995 | Bancroft . |
| 5,460,527 | 10/1995 | Kittelsen . |
| 5,513,656 | 5/1996 | Boyd, Sr. . |
| 5,566,684 | 10/1996 | Wagner . |
| 5,584,687 | 12/1996 | Sullivan . |
| 5,718,575 | 2/1998 | Cross, III . |
| 5,836,761 | 11/1998 | Belvedere . |

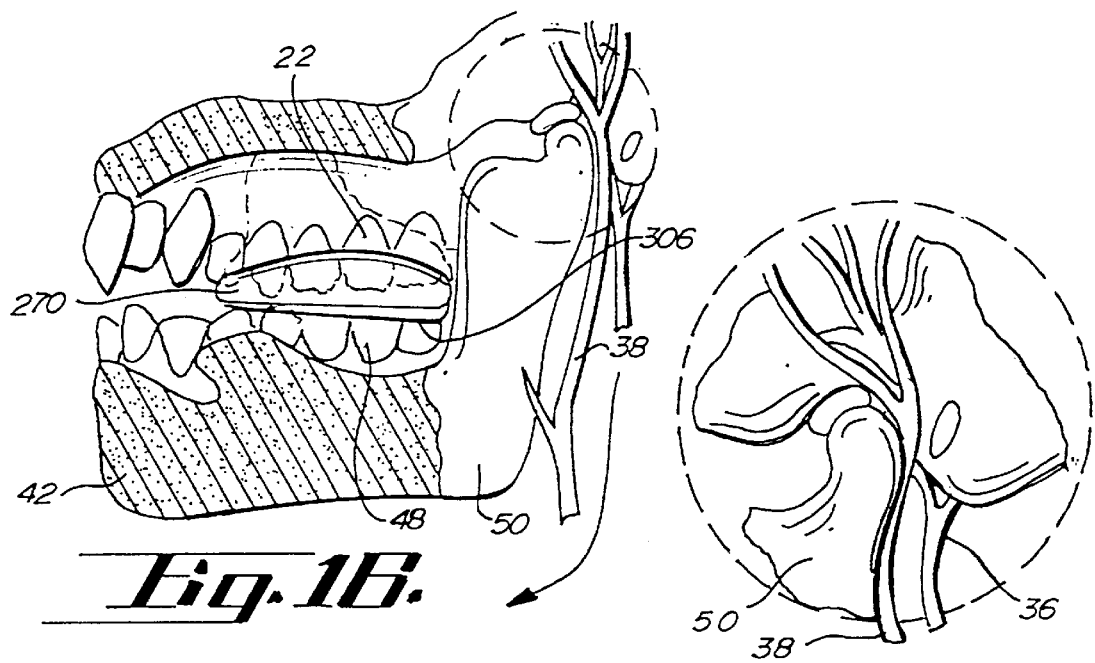
_Fig. 16._
_Fig. 17._
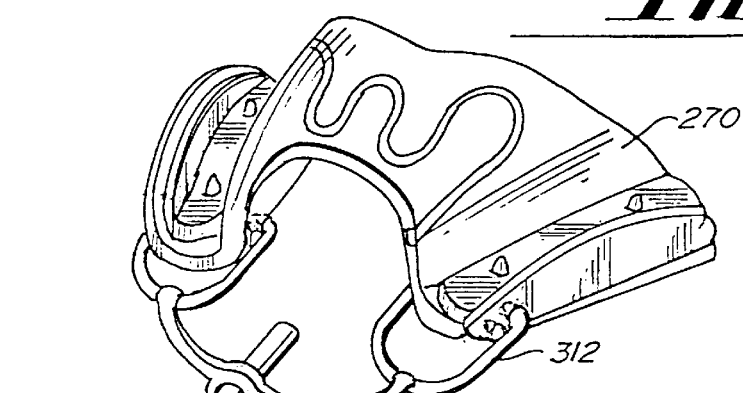
_Fig. 19._
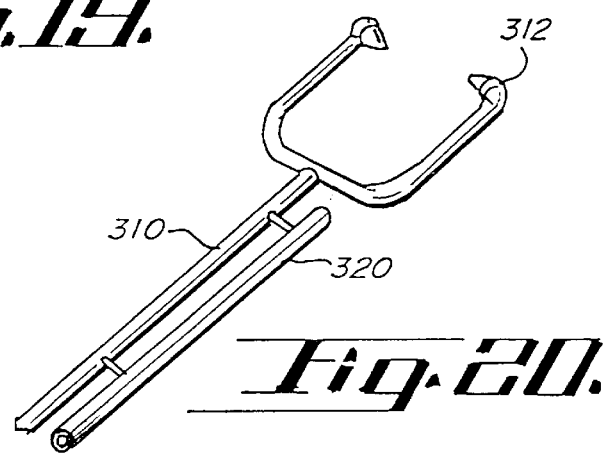
_Fig. 20._

6,012,919

TRIPLE COMPOSITE PERFORMANCE ENHANCING DENTAL APPLIANCE

This application is a continuation of co-owned patent application Ser. No. 09/022,319, filed on Feb. 11, 1998, now U.S. Pat. No. 5,865,619, which is a continuation-in-part of co-owned U.S. Ser. No. 08/764,900 filed Dec. 16, 1996, issued on Feb. 17, 1998, now U.S. Pat. No. 5,718,575 which is a continuation-in-part of co-owned U.S. Ser. No. 08/375,921 filed Jan. 19, 1995, issued on Dec. 17, 1996, now U.S. Pat. No. 5,584,687, which is a continuation of patent application Ser. No. 08/104,489, filed on Aug. 9, 1993, now abandoned, all of which share common inventorship.

BACKGROUND OF THE INVENTION

This invention relates generally to a performance enhancing and force absorbing dental appliance for use by athletes, and more particularly to such an adjustable, customizable appliance that spaces apart the teeth to absorb shock and clenching stress, to space apart the anterior teeth of the lower and upper jaws to facilitate breathing and speech, to lessen condyle pressure, force and impact upon the cartilage and temporomandibular joints, the arteries and the nerves, and to further increase body muscular strength and endurance.

Almost all athletes, such as body builders, weight lifters, baseball batters, golfers, football players, hockey players and bowlers, clench their teeth during exertion which results in hundreds of pounds of compressed force exerted from the lower jaw onto the upper jaw. This clenching force is unevenly transmitted through the jaw structure into the connective tissues and muscles of the lower jaw and further into the neck and back. This can result in headaches, muscle spasms, damage to teeth, injury to tie temporomandibular joint, and pain in the jaw. Furthermore, clenching the teeth makes breathing more difficult during physical exercise and endurance when breathing is most important.

The natural inclination to clench the jaw during physical exertion is impossible to avoid. One theory is that this is an ancient reflex designed to protect the caveman's jaw from displacement or fracture. An injury to ancient man's jaw meant almost certain death from starvation. Man still instinctively clenches his teeth to lock his jaw into a safe position during aggression or physical activity to protect his jaw. But when the teeth are clenched, the body puts an upper limit on one's strength so that one can't overclench and damage one's teeth and jaw structures.

There are over 60 million overweight Americans today. Spending in the diet aid category equals $1.06 billion annually. Research shows that use of a dental appliance to prevent damage to the teeth during clenching helps to increase the productivity of an aerobic workout by increasing endurance and muscle activity and therefore calorie burn.

More than 80% of the population has some measure of improper jaw alignment, causing painful chewing, tooth grinding, migraine headaches, stress or several of these problems at once. The temporomandibular (TM) artery runs directly through the TM joint. This main artery carries oxygenated blood to the arteries in the face and head. When the TM joint is properly balanced, blood flows freely to these areas, which is believed to lessen the incidence of headache and stress. When the TM joint is out of balance or improperly aligned, undue stress is placed on this vital artery and the corresponding muscle groups.

Each year, reports the Journal of the American Dental Association, dentists make approximately 3.6 million anti-bruxing devices for their tooth grinding patients. At an average cost of $275 (but sometimes much higher), this equates to a one billion dollar market. Nocturnal tooth grinding is a major pain—powerful enough to crack a walnut at 250 pounds per square inch, the pressure is ten times the force registered during normal chewing. Bruxing causes the teeth to wear down at odd angles, affecting the shape of the face, causing migraine headaches and muscle soreness and aggravating TMJ disorders.

The market for over-the-counter analgesics in the U.S. was $2.91 billion in 1996. An estimated 18 million people suffer from migraine headaches, another 6 million form back and neck pain. While almost 3 million Americans are treated annually by pain clinics, many more remain in need due to inadequate insurance or denial of benefits for such treatment. Studies have shown that increasing the blood flow to the arteries of the face can help reduce headache pain. Repositioning the jaw by a dental appliance to alleviate stress and pain acts as a drug-free remedy to millions of stress and headache sufferers by temporarily restoring blood flow to the face and head.

It is well known that the birthing process creates a tremendous amount of physiological and psychological stress upon the mother. In fact, pregnant women go through weeks, if not months, of physical exercise to prepare them for the exertions necessary during the birth of their child. The actual birthing process is very analogous to athletes as women about to give birth may very well clench their teeth during the exertion of labor.

Rehabilitation relative to heart attacks, operations and injuries also require exertion and can be facilitated by an increased blood flow to the brain and return back to good conditioning with exercise.

Snoring occurs when the mouth is open and the tongue moves back into the throat. This causes the airway passage to narrow which increases the likelihood of snoring. It is known that moving the condyle of the lower jaw forward in a way will increase the airway and assist in the elimination of snoring.

It is believed that consciousness and the ability to focus is increased with an object in the mouth. This causes one to salivate, focus and be more awakened with improved concentration, hand eye coordination, and even thought process which otherwise would be non-voluntary reactions.

There is a need for an adjustable, customizable performance enhancing and force absorbing dental appliance for the mouth of a physically active, birthing or rehabilitating individual which will absorb shock and clenching stress otherwise transferred from the connective tissues, the muscles and lower jaw to the upper jaw, neck and back, will space apart the anterior teeth of the lower jaw from the anterior teeth of the upper jaw to facilitate breathing and speech, and will lessen condyle pressure, force and impact upon the cartilage, and temporomandibular joints, arteries and the nerves. There is also a need for an adjustable, customizable dental appliance that will increase blood flow to the face and head by repositioning the condyle of the jaw away from the TM artery. There is also a need for a personalizable dental appliance to reduce stress, bruxing wear on the teeth and snoring. The appliance should also increase rehabilitation and consciousness.

SUMMARY OF THE INVENTION

A performance enhancing and force absorbing dental appliance adapted to lie within the mouth of an athlete consists of an occlusal posterior pad made of triple composite material with a base having a top layer of impressionable material, an intermediate layer of hard material and a somewhat impressionable bottom layer, engageable with the occlusal surfaces to space apart the upper and lower teeth, to absorb shock and clenching stress. An adjustable arch adapted to expand and contract to be molded to the palate is provided connecting the posterior pads together within the mouth and out of the way of the tongue to maintain the position of the occlusal posterior pads within the mouth during use and to prevent loss of the pads such as by swallowing. An optional expandable stiffener may be embedded in the arch. Optional protrusions extend from the bottom layer through the intermediate layer and top layer to engage the central fossae of the molar teeth.

A principal object and advantage of the present invention is that the appliance protects the teeth, jaws, gums, connective tissues, back, head and muscles from teeth clenching forces typically exerted during athletic activity and birthing.

Another object and advantage of the present invention is that it facilitates breathing and speech during strenuous physical activity such as in power lifting or body building.

Another object and advantage of the present invention is that the appliance places the lower jaw in the power position moving the condyle downwardly and forwardly away from the nerves and arteries within the fossae or socket to raise body muscular strength, greater endurance and improved performance by the appliance user.

Another object and advantage of the present invention is that the appliance is customizable to fit the indentations of the upper and lower posterior teeth and personalizable or custom formable in the arch to fit the palate stricture of the user.

Another object and advantage of the present invention is that the palate's formable and adjustable arch is preferably made of an impressionable material which will permit the user to refit the appliance should the appliance become bent, kinked, twisted or otherwise distorted.

Another object and advantage of the present invention is that it allows the wearer to increase effort and calorie burn during a workout by preventing the clenching reflex from limiting bodily strength and endurance.

Another object and advantage of the present invention is that it prevents grinding of the teeth (bruxing).

Another object and advantage of the present invention is that helps to alleviate pain such as migraine headache by properly positioning the lower jaw and increasing the blood flow through the temporomandibular artery and associated circulatory and nerve systems.

Another object and advantage of the present invention is that allows a woman to increase the force with which she bears down during labor contractions, without harming the teeth and associated oral structures.

Another object and advantage of the present invention is that it assists in the rehabilitation process of recovering from injury or heart attacks by increasing the flow of blood and oxygen to the brain.

Another object and advantage of the present invention is that it increases consciousness and is believed to have a systemic action that can alter non-voluntary reactions to external stimuli to make the appliance wearer more conscientious, focused, awake and ready.

Another object and advantage is that the present invention reduces snoring by moving the condyle forward and further opening up the airway passage.

Another object and advantage of the present invention is that it has a somewhat impressionable bottom layer engaging the lower teeth, the layer being wedge-shaped and thinner in the front to help move the condyle downwardly and forwardly away from the TM joint.

Another object and advantage of the present invention is that it includes a handle for dipping the device into warm water and then inserting the device in the mouth.

Another object and advantage of the present invention is that includes a straw for sucking cold water into the mouth to cool the device after softening it.

Other objects and advantages will become obvious with the reading of the following specification and appended claims with a review of the Figures.

BRIEF DESCRIPTION OF THE DRAWINGS

FIG. 16 is a side elevational view of the jaw structure showing the third embodiment of the dental appliance in place.

FIG. 17 is a detail of the phantom circled area of FIG. 16.

FIG. 19 shows an optional handle attached to the appliance, the handle having an internal core for use as a straw.

FIG. 20 shows the handle with a removable straw attached to the handle.

DETAILED SPECIFICATION

Figure 1:
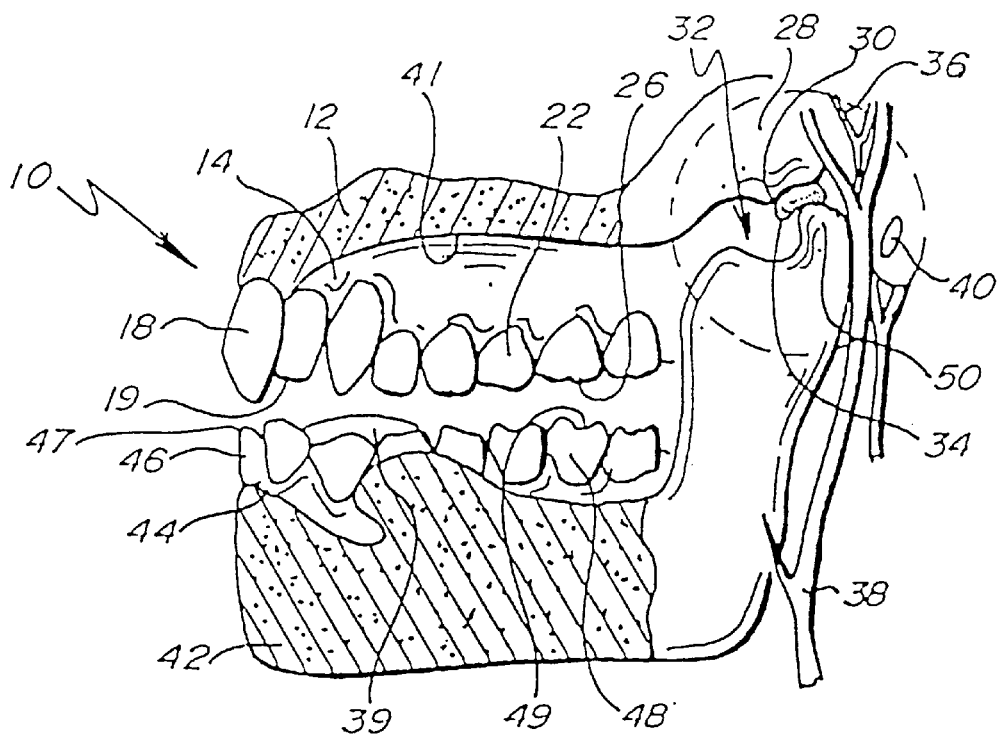
FIG. 1 is a maxillary mandibular buccal or partial side elevational view of the jaws and temporomandibular joint of the user of the dental appliance of the present invention.
Figure 1A:
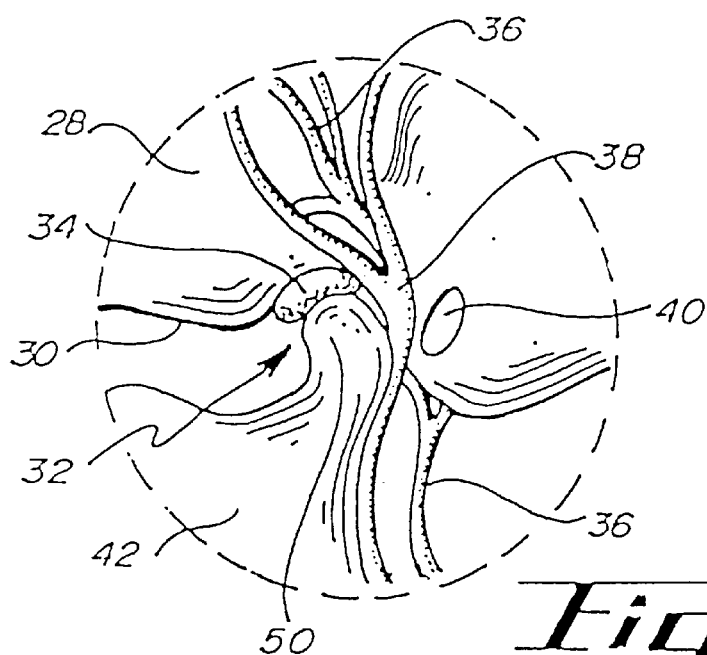
FIG. 1A is an enlarged view of the temporomandibular joint portion of FIG. 1.
Figure 6:
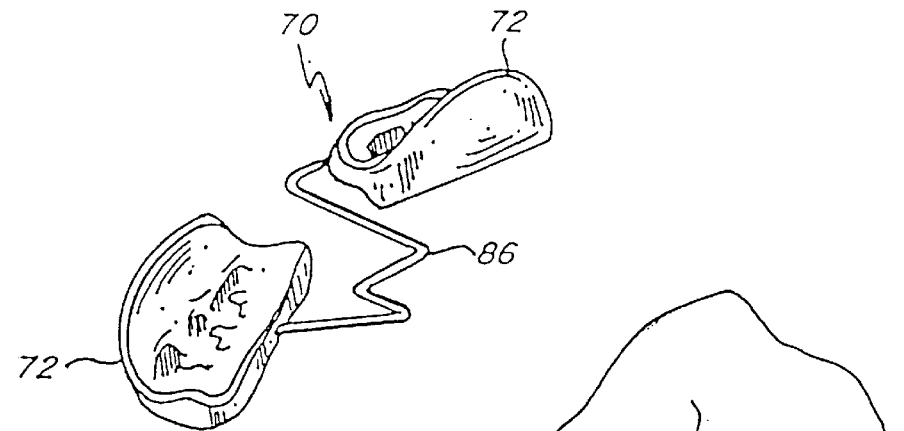
FIG. 6 is a perspective view of the appliance arch bent out of shape.
Figure 7:
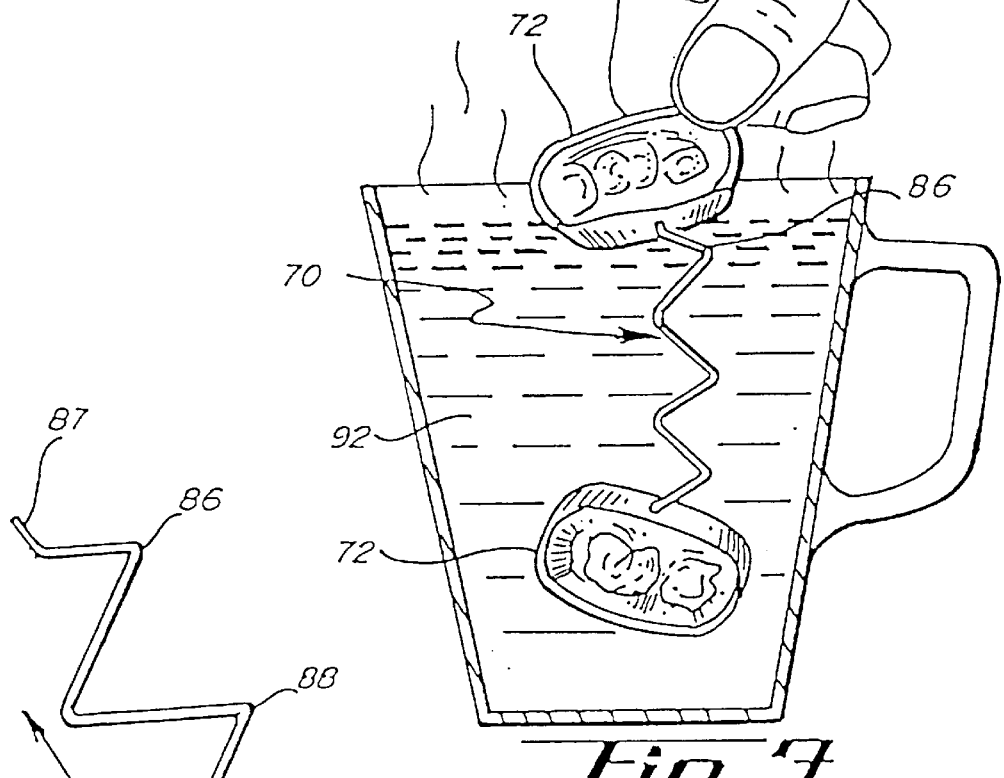
FIG. 7 is an elevational view of the arch being submersed in warm water for straightening.

To understand the structural features and benefits of the dental appliance 70 of the present invention, some anatomy will first be described. Referring to FIGS. 1 and 1A, the user or athlete has a mouth 10 generally comprised of a rigid upper jaw 12 and a moveable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, supports anterior teeth (incisors and canines) 18 which have incisal or biting surfaces 19. The gum tissues 14 and the bone thereunder also support posterior teeth (molars and bicuspids) 22 which have cusps or biting surfaces 26.

Referring to one side of the human head, the temporal bone 28 is located upwardly and rearwardly of the upper jaw 12 and is in the range of 1/16 to 1/32 inch thick. The articular eminence 30 forms the beginning of the fossa 32 or the socket of the temporomandibular joint 32 and 50. Rearwardly and posteriorly to the articular eminence 30 is located cartilage 34. Through the temporomandibular joint 32 and 50 pass the auriculo-temporalis nerve 36 and the supra-temporo artery 38. Posteriorly to this structure is located the inner ear 40. Within the mouth is located tongue 39 and the roof or hard palate 41 which terminates rearwardly into the soft palate.

The movable jaw or mandible 42 supports a bone covered by gum tissue 44 which further supports anterior teeth (incisors and canines) 46 with incisal or biting surfaces 47 and posterior teeth (molars and bicuspids) 48 with occlusal biting surfaces 49. The condyle 50 of the lower jaw 42 forms the ball of the temporomandibular joint 32 and 50. The anatomical structure is the same for both sides of the head.

Repeated impacts, collisions, blows, stress or forces exerted on the movable lower jaw 42 result in excessive wearing forces upon the condyle 50 and the cartilage, meniscus, or disc 34—typically resulting in bone deterioration on the head of the condyle or slippage and compressive damage of the cartilage 34. Thereafter, the lower jaw 42 may be subject to irregular movement, pain, loss of comfortable range of movement and clicking of the joint 32 and 50.

The auriculo-temporalis nerve 36 relates to both sensory and motor activity of the body. Any impingement or pinching of this nerve 36 can result in health problems as previously mentioned. The supra-temporal artery 38 is important in that it provides blood circulation to portions of the head. Impingement, pinching, rupture or blockage of this artery 38 will result in possible loss of consciousness and reduced physical ability and endurance due to the restriction of blood flow to portions of the brain. Thus, it is extremely important to assure that the condyle 50 does not impinge upon the auriculo-temporalis nerve 36 or the supra-temporal artery 38.

It is also important to note that the temporal bone 28 is not too thick in the area of the glenoid fossae. Medical science has known that a sharp shock, stress, or concussive force applied to the lower jaw 42 possibly could result in the condyle 50 protruding through the glenoid fossa of the temporal bone 28, thereby causing death. There is a suture line (growth and development seam) in the glenoid fossae, resulting in a possible weakness in the fossae in many humans. This incident rarely, but sometimes, occurs with respect to boxing athletes.

Referring to FIGS. 1B through 7, the power enhancing and shock absorbing dental appliance 70 may generally be seen. The appliance 70 has occlusal pads 72 which are suitably made of thermoplastic materials such as copolymers of ethylene and vinyl acetate and other FDA approved materials. It has been found that ethylene vinyl acetate (EVA) is a commercially available compound and approved for oral use by the Food and Drug Administration. The occlusal pads 72 are connected arch 86.

Figure 1B:
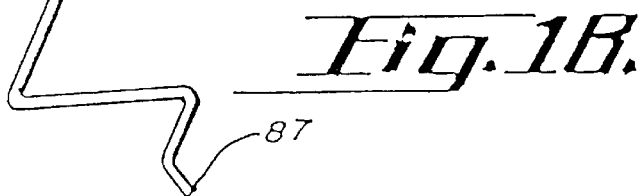
FIG. 1B is a perspective view of the appliance arch of shape memory alloy.

Referring specifically to FIG. 1B, arch 86 in its desired form may be seen. The arch end 87 are molded into occlusal pads 72 when they are formed. The arch is suitably made of a shaped memory alloy suitably of nickel and titanium, preferably in the range of 55 percent nickel and 45 percent titanium. As said, connecting band or wire 86 is preferably made of a titanium base alloy. The stabilizing alloying elements can include manganese, iron, chromium, cobalt, nickel, copper, aluminum, tin and zirconium. Such alloys may also be alpha-titanium or beta-titanium. These alloys exhibit ultra-elasticity and can be made with a memory shape which the wire alloy 86 will return to upon heating. Such a wire product may be obtained from Ultimate Wireforms, Inc., 200 Central Street, Bristol, Conn. 06010. The arch 86 may also be made of stainless steel, annealed wire, braided wire or electrical-like wire.

The arch 86 is in a wire form, which may be 0.02 to 0.05 inches in diameter. 0.032 inches in diameter is found to be optimal. The wire 86 has an undulating or accordion appearance as to permit longitudinal expansion and contraction along ↕A. Thus, the wire has bends 88 along its length. The ends 87 of the arch wire 86 preferably are looped, hooked or form some type of eyelet as to be readily securable when molded into the occlusal pads 72.

The arch wire 86 may have one temperature transition range or multiple temperature transition ranges between the bends 88 and straight portions of the wire 86. For example, the bent 88 end of hooked end portions 87 suitably may have a higher temperature transition range of 110° to 190° while the straight portions between the bends 88 may have a higher temperature transition range of 140° to 220°. Presently, applicant has found the bends 88 suitably should have a temperature transition range of approximately 150° while the straight portions of wire 86 have a temperature transition temperature of 180°. With the lower transition temperature in the bend 88 areas, the shaped memory alloy nickel titanium wire arch 86 is more stiff than the straight portions of the wire 86.

Figure 2:
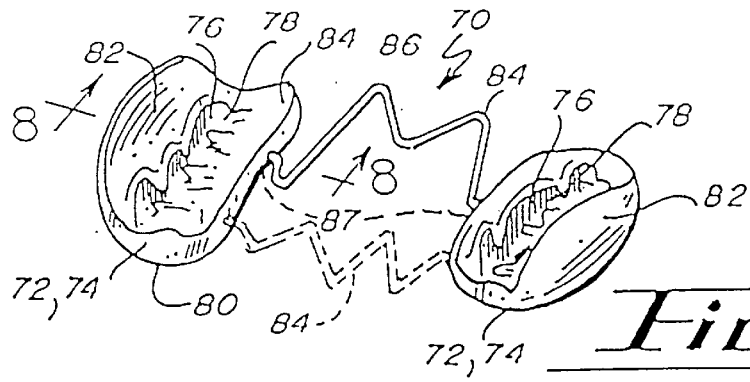
FIG. 2 is a perspective view of the performance enhancing and force absorbing dental appliance.
Figure 3:
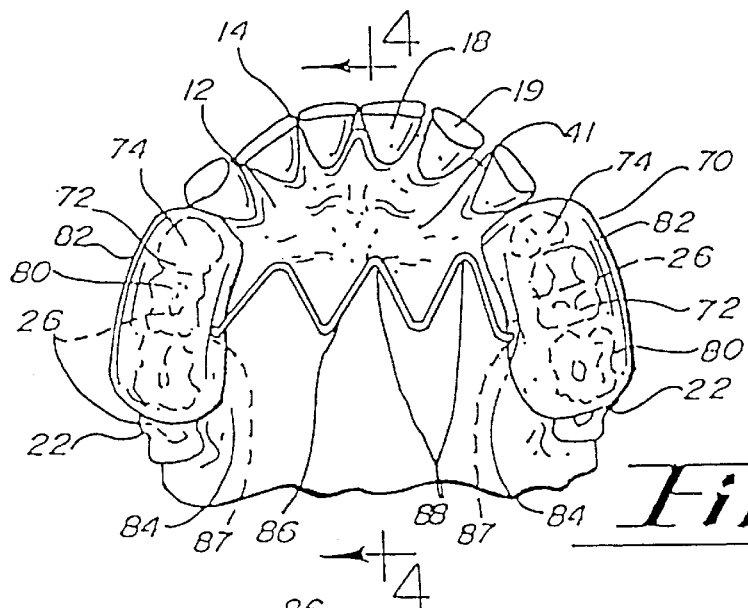
FIG. 3 is a bottom plan view of the upper jaw structure and teeth with the dental appliance in place.
Figure 4:
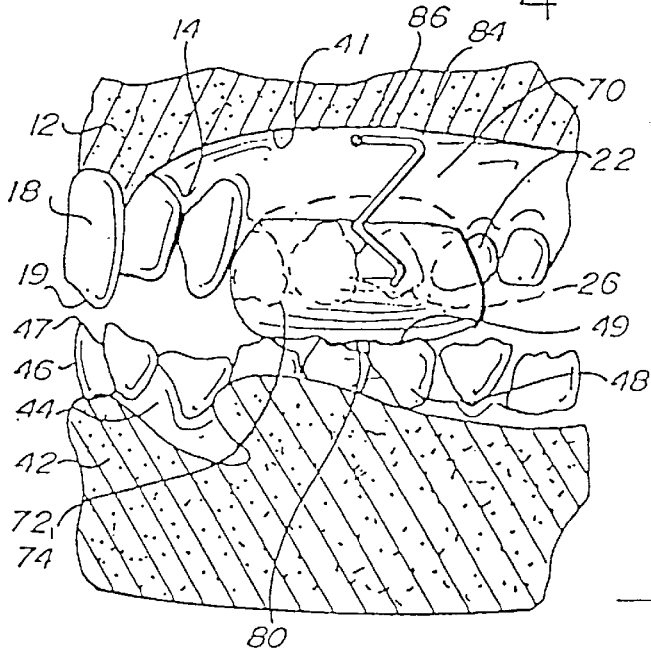
FIG. 4 is a cross-sectional view taken along lines 4—4 of FIG. 3.

Upon the arch structure 86 becoming distorted, it simply may be heated with the boiling water or heat from a match or lighter to spring the arch 86 back into its memorized structure. As can be seen in FIG. 2, the hook or eyelet ends 87 of the arch 86 are molded into the posterior paths 72.

The appliance 70 has posterior occlusal pads 72 each including a base 74 having a fitted top surface 76 with teeth indentations 78 for receiving the posterior teeth 22 of the upper jaw 12 as further explained below. The base 74 has a bottom surface 80 also somewhat conformable to the lower jaw posterior teeth 48. Extending upwardly from base 74 is the labial or buccal wall 82 and lingual wall 84.

Figure 5:
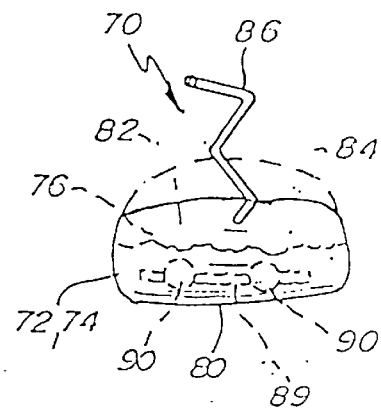
FIG. 5 is a cross-sectional view similar to the appliance in FIG. 4 showing another embodiment.

Optionally, the posterior occlusal pads 72 may have cushions 89 embedded therein appropriately with enlarged portions 90 (FIG. 5). The cushions 89 should suitably be made of a thermoplastic rubber such as that marketed under the trademark Kraton® which is marketed by GLS Plastics of 740B Industrial Drive, Cary, Ill. 60013. This thermoplastic rubber is unique in that it is injection-moldable, FDA approved and readily adheres with copolymers of ethylene and vinyl acetate. Furthermore, the thermoplastic rubber has a melting or softening point significantly higher than that of EVA which will facilitate custom fitting of the dental appliance 70 to the user or athlete's mouth 10. Furthermore, the thermoplastic rubber, unlike copolymers of ethylene and vinyl acetate, exhibits high resilience, low compression, shape maintenance and shock absorption, attenuation and dissipation. Virtually all rubbers exhibit these physical characteristics which may be utilized for the elastomeric cushion 89.

The enlarged portions 90 of embedded cushion 89 are arranged suitably to be in the bicuspid or molar regions of the teeth 22 and 49. The enlarged portions 90 may take the form of spheres, columns or knobs.

The cushion 89, and optionally the enlarged portions 90, together with the posterior occlusal pads 72 cause the mandible or lower jaw 42 to slide forwardly and slightly downwardly while fitting the dental appliance 70. Also, the condyles 50 are moved downwardly and away from the fossae or sockets 32 without the need for exotic devices and/or measurements, articulation, etc. Furthermore, the posterior cushions 89 and optional enlarged portions 90 assure proper fitting of the appliance 70 when the pads 72 are softened thereby prohibiting the user or athlete from biting too deeply into the soft EVA material of the occlusal pads 72 during fitting.

As is also to be appreciated, the occlusal pads 72 space apart the anterior teeth 18 and 46 while the arch 86 is to be clear of the tongue 39 and the tongue can move freely below the palate 41 which will readily permit the wearer to easily breathe in power fashion as well as convey the ability to speak clearly.

For fitting the appliance 70, the arch 86 may be intermediately bent and grasped thereat and may be momentarily submersed suitably in boiling water for a period of time prescribed in instructions of ten seconds to two minutes. Thereafter, the appliance 70 is immediately placed onto the posterior teeth 22 of the upper jaw 12. Next, the lower jaw 42 is positioned forwardly or anteriorly in a range of one to four millimeters as the posterior teeth 48 of the lower movable jaw 42 are positioned on the bottom surface 80 of appliance 70. The wearer or user then applies suction between the upper jaw 12 and the appliance 70 while packing the appliance 70 with the hands along the cheeks adjacent the posterior teeth 22 of the upper jaw 12.

Next, the user may feel along the arch 86 to determine where the arch is not lined along the palate 41. The user takes the appliance 70 out of the mouth and adjusts the lateral length of the arch 86 suitably by stretching or condensing as shown along ↕A in FIG. 1B. The user next forces the arch 86 upwardly as to permit the arch 86 to properly lie along the palate 86. After this fitting, the appliance 70 is ready for repeated use.

Extending beneath the arch 86 and defined by the arch 86 and the lingual walls 84 of the pads 72 is a tunnel 87. The tunnel 87 is open anteriorly and posteriorly to allow unobstructed movement of the tongue anteriorly and posteriorly.

By this action, the user of the appliance 70 will have correct jaw posture for athletic participation once fitting has been completed and the appliance 70 has cooled. The posterior teeth 48 of the lower jaw 42 will properly index upon the bottom surfaces 80 of the occlusal pads 72. Should the cushions 88 optionally be embedded within the pads 72, they will absorb, attenuate and dissipate shock and stress forces, such as created by clenching. Furthermore, the user will experience increased endurance, performance and muscular freedom due to the power positioning and posture of the TMJ joints 32 and 50.

The user from time to time may not protect the appliance 70 by placement and storage within a container. For instance, the appliance 70 may be placed in a gym bag or golf bag which will permit the arch 86 to become that crushed or otherwise severely distorted shown in FIG. 6. To correct this deformation and to refit the arch 86, the user simply exposes the arch 86 to some heating means, such as hot water 92 shown in FIG. 7. Alternatively, the flame of a lighter or match similarly will permit the shaped memory alloy wire arch 86 to spring back to its original shape for a refitting of the arch 86 along the palate 41.

Figure 8:
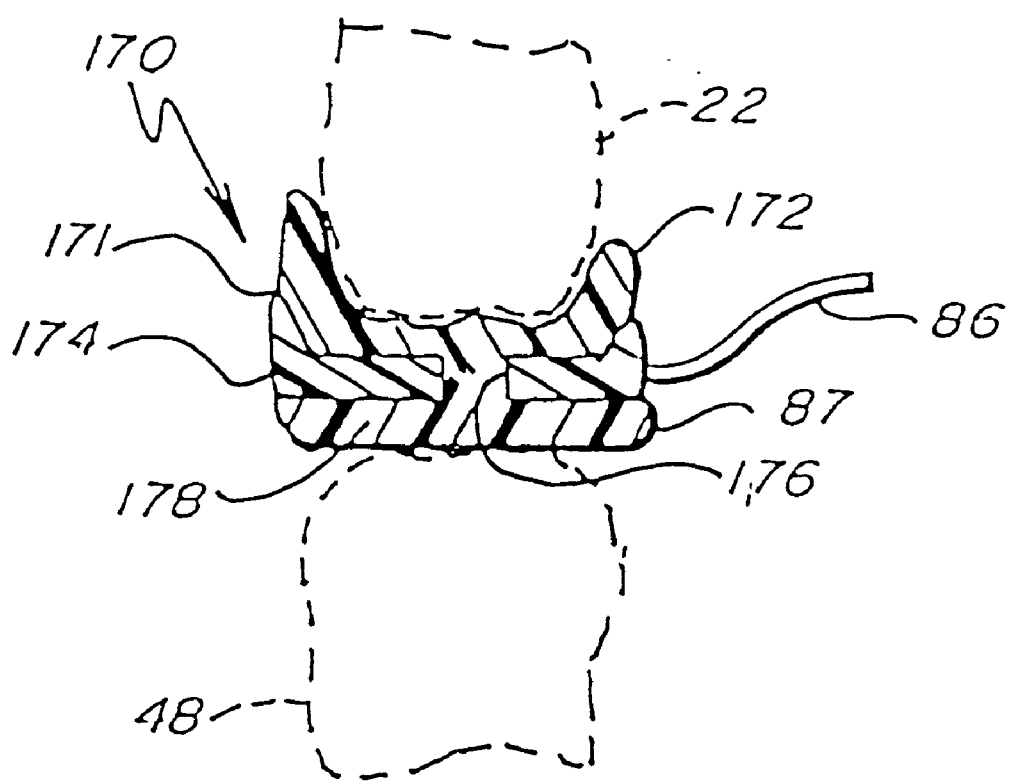
FIG. 8 is a cross of the modified arch taken along lines 8—8 of FIG. 2.
Figure 9:
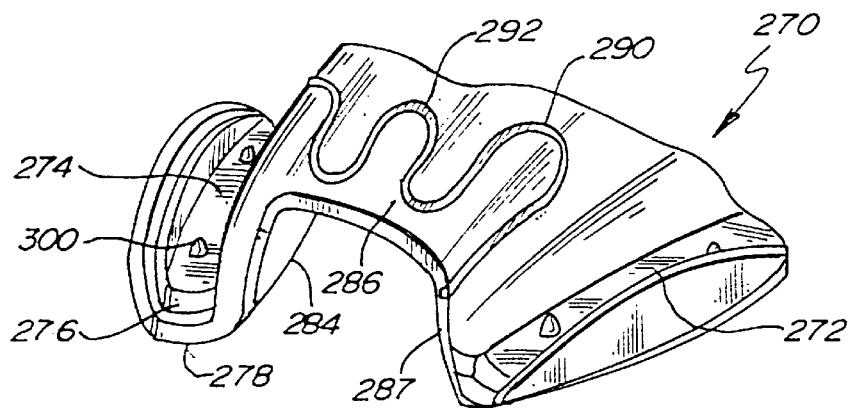
FIG. 9 is a perspective view of a third embodiment of the performance enhancing and force absorbing dental appliance.
Figure 10:
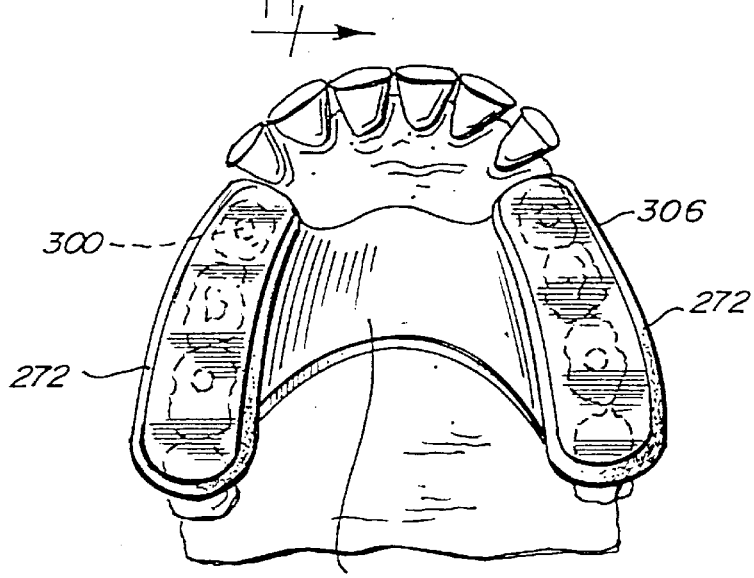
FIG. 10 is a bottom plan view of the upper jaw structure and teeth with the third embodiment of the dental appliance in place.
Figure 11:
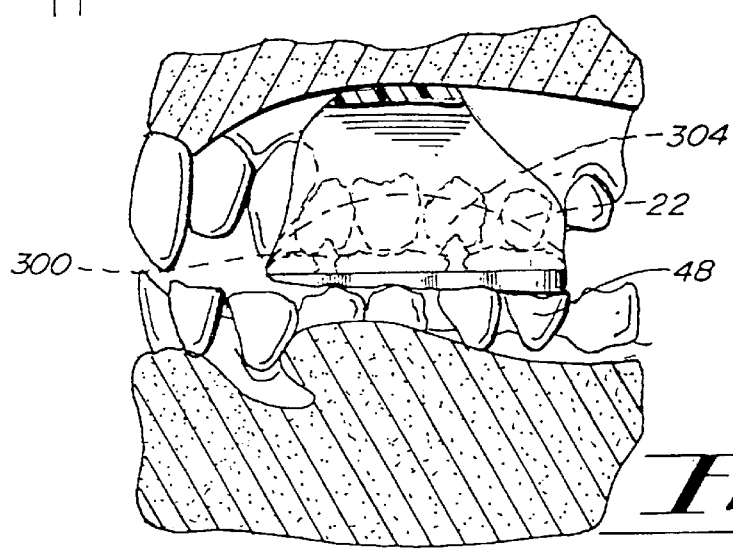
FIG. 11 is a cross-sectional view taken along lines 11—11 of FIG. 10.
Figure 12:
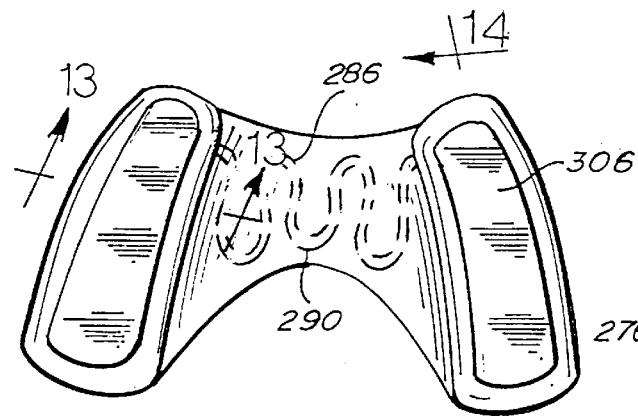
FIG. 12 is a bottom plan view of a third embodiment of the dental appliance with some internal structure shown in phantom.
Figure 13:
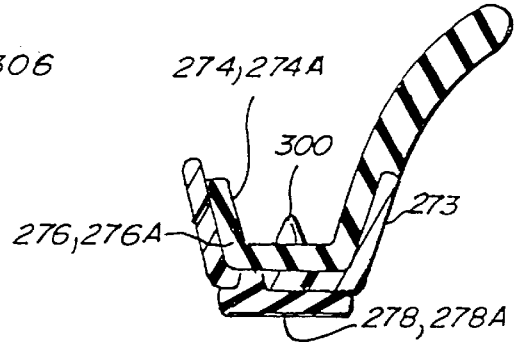
FIG. 13 is a cross-sectional view taken along the lines 13—13 of FIG. 12.
Figure 14:
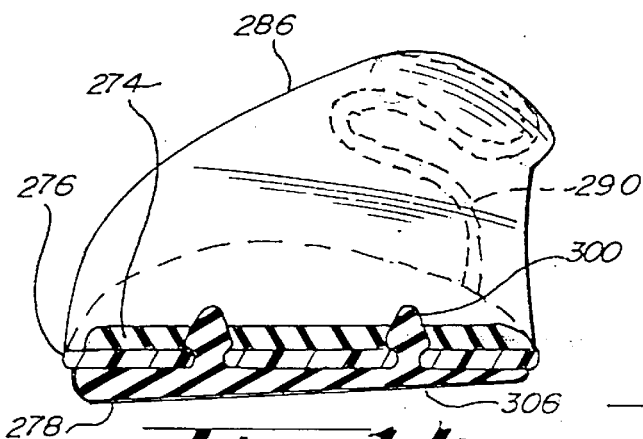
FIG. 14 is a cross-sectional view taken along the lines 14—14 of FIG. 12.

FIG. 8 shows a modified appliance wherein the occlusal pad 171 similar to the occlusal pad 72 of the earlier embodiment is made from a triple composite. The top impressionable layer that is softenable by heat is suitably made of approximately 50% of a polycaprolactone polymer and a 50% composition of 150 ethylene vinyl acetate or EVA. The polycaprolactone polymer is marketed under the name Hydroplastic™ and may be obtained from TAK Systems, P.O. Box 939, East Wareham, Mass. 02538 (disclosed in U.S. Pat. No. 5,112,225). However, the top impressionable layer 172 may be also made solely of EVA.

The intermediate layer is suitably a thermoplastic or thermoplastic rubber such as polyethylene, polypropylene, styrene or the like that is more rigid to securably hold the looped end 87 of the wire or band 86 in place. The intermediate layer 174 has an aperture 176 therethrough to permit an inner locking of the moldable top impressionable layer 172 to the somewhat impressionable bottom or sole layer 178. The bottom or sole layer 178 is suitably made of this thermoplastic elastomer such as a Kraton® and EVA composition. Kraton® is marketed by GLS Plastics of 740B Industrial Drive, Cary, Ill. 60013, and approximately a 50% portion of 150 EVA.

Thus, when the occlusal pad 171 is immersed in hot water, the top layer 172 becomes fairly impressionable while the bottom layer 178 becomes somewhat impressionable to facilitate inter digitation of the upper and lower teeth 22 and 48.

FIGS. 9–20 shows a perspective view of a third embodiment of the dental appliance 270 of the present invention.

As can be seen, the dental appliance 270 comprises a pair of occlusal posterior pads 272 made of a triple composite material with a base 273 having a top layer 274 of an impressionable material 274A, an intermediate layer 276 of a hard material 276A, and a bottom layer 278 of a somewhat impressionable material 278A. Herein, "somewhat impressionable" refers to a material with a degree of softness intermediate between the hard material 276A and the impressionable material 274A.

The occlusal pads 272 are engageable with the occlusal surfaces of the upper posterior teeth 22 and lower posterior teeth 48 to space apart the teeth, to absorb shock and clenching stress otherwise transferred from the connective tissues, the muscles and the lower jaw 42 to the upper jaw 12, neck, and back, to space apart the anterior teeth 46 of the lower jaw from the anterior teeth 18 of the upper jaw to facilitate breathing and speech, and to lessen condyle 50 pressure, force, and impact upon the cartilage 34, temporomandibular joints 32 and 50, arteries 38 and nerves 36.

A continuous vertical arch 286 open anteriorly and posteriorly, extends from the top layers 274 of the occlusal posterior pads 272 and is constructed from the impressionable material 274A. The arch 286 is adapted to expand and contract to be molded to the palate 41 because it is made of the impressionable material 274A. Further, the arch 286 is adapted to lie along the palate 41 out of the way of the tongue 39 and extends directly across to and connects the posterior pads 272 together within the mouth and out of the way of the tongue to maintain the positions of the posterior pads 272 within the mouth and to prevent the loss of the pads 272 such as by swallowing.

A tunnel 287 extends beneath the arch 286 and is defined by the arch 286 and the lingual walls 284 of the occlusal posterior pads 272. The tunnel 287 is open anteriorly and posteriorly to allow unobstructed movement of the tongue 39 anteriorly and posteriorly.

The dental appliance 270 may also preferably comprise a stiffener 290 embedded in the arch 286. Preferably, the stiffener 290 is expandable and contractible, thereby following and supporting the arch 286 as the arch 286 is molded to the palate 41. The stiffener 290 reinforces the arch 286 and prevents the arch 286 from sagging completely out of shape when it is subjected to heat during the fitting process.

In the preferred embodiment, the stiffener 290 is serpentine, further comprising a series of loops 292 winding back and forth across the arch 286. It will be recognized that these loops 292 allow the stiffener 290 to expand and contract. Preferably, the stiffener 290 is constructed of the hard material 276A and is continuous with the intermediate layer 276.

Figure 18A:
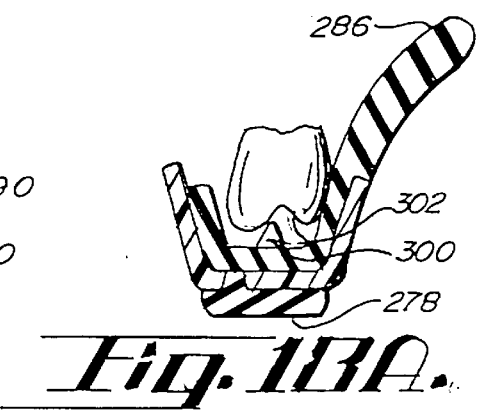
FIGS. 18A and 18B are schematics showing the used of the small protrusions in engaging the central fossae of the molar teeth.
Figure 18B:
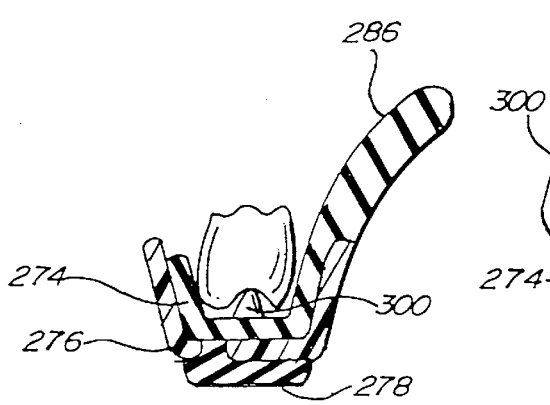
Figure 15:
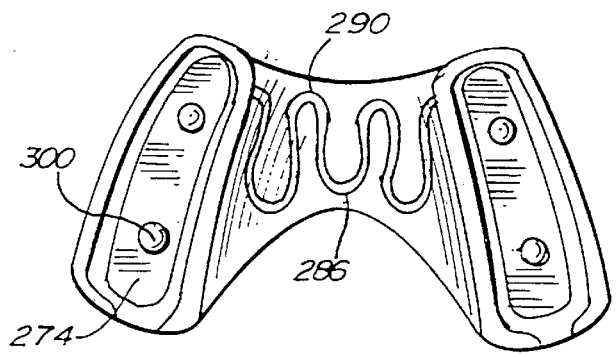
FIG. 15 is a top-plan view of a third embodiment of the dental appliance.

The dental appliance 270 may also preferably comprise a plurality of protrusions or cones 300 adapted to engage the central fossae 302 of the molar teeth 304 of the upper jaw 12. In this manner, as shown in FIG. 18A, when the wearer bites down on the appliance 270, the protrusions 300 are forced into the central fossa 302, thus positioning the appliance 270 from the out of line position shown in FIG. 18A to the correctly aligned position shown in FIG. 18B. This positioning is essential so that the bottom layer 278 of the pads 272 is in line with the teeth, as will be described below.

In the preferred embodiment, the protrusions 300 are constructed of the somewhat impressionable material 278A and extend from the bottom layer 278 through the intermediate layer 276 and the top layer 274. In this manner, the protrusions 300 also serve to strengthen the layers 274, 276, 278 and lock the layers together. The protrusions also help prevent the arch 286 from contorting.

The protrusions 300 also help to maintain spacing between the teeth and help to manipulate the lower jaw 72 forwardly.

Preferably, the bottom layer 278 is wedge shaped, as shown in the Figures, being thicker posteriorly and thinner anteriorly. As can be seen in FIGS. 16 and 17, this wedge shape forces the condyle 50 of the law 42 to move forwardly and downwardly away from the auricula-temporalis nerve 36 and the supra-temporal artery 38 and the suture line in the glenoid fossae, as indicated by the arrow in FIG. 16. This places the jaw 72 into the "power position", alleviating stress on through the artery and increasing blood flow through the artery. It has been found that this increased blood flow helps to alleviate headache pain and stress.

In order for this wedge shape to work properly, the power plates 306 or the bottom layer 278 must be centered between the teeth. As discussed above, the protrusions 300 help to ensure this centering.

In the preferred embodiment, the impressionable layer 274 is softenable by heat. In this regard, the impressionable layer 274 preferably comprises about 50% by weight of a polycaprolactone polymer and about 50% by weight of ethylene vinyl acetate. The polycaprolactone polymer is marketed under the name Hydroplastic™ and may be obtained from TAK Systems, P.O. Box 939, East Wareham, Mass. 02538 (disclosed in U.S. Pat. No. 5,112,225). However, the top impressionable layer 274 may be also made solely of EVA.

Alternatively, the impressionable layer may be hardened by another catalyst. For example, the impressionable material may be a light-curing resin which is soft when in the dark but becomes hardened when exposed to light. Such a light-curing resin may preferably consist essentially of methyl methacrylate, chlorosulfonated polyethylene, fluoridated methacrylate, methacrylic acid, and photo initiators. A suitable light-curing resin is available under the name Spectra Tray from Ivoclar AG, Bendererstrasse 2, FL9494 Schaan/Liechtenstein.

The intermediate layer 276 is suitably a thermoplastic or thermoplastic rubber such as polyethylene, polypropylene, styrene or the like that is more rigid. The bottom layer 278 is suitably made of a thermoplastic elastomer such as a Kraton® and EVA composition. Kraton® is marketed by GLS Plastics of 740B Industrial Drive, Cary, Ill. 60013. Preferably, the bottom layer 278 comprises about 50% Kraton® and approximately a 50% portion of 150 EVA.

Suitably, a handle 310 may be provided, for example, to dip the appliance 270 into warm to hot water to soften the impressionable material 274 and to allow the appliance to be fitted to the mouth. The handle may attach to the appliance 270 by any suitable method. For example, the handle may be formed with the appliance and thinner areas adjoining the appliance may allow the handle to be broken off. Preferably, the handle 310 has biased pinchers or grips 312 which frictionally engage the appliance 270.

A straw 320 may also be provided to allow the wearer to suck cold water into the mouth to harden the impressionable material 274A after fitting. The straw 320 may be a hollow portion in the handle 310, as shown in FIG. 19. Alternatively, the straw 320 may be attached to the handle 310 and removed for use, as shown in FIG. 20.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

We claim:

1. A performance enhancing and force absorbing dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the socket forming the temporomandibular joints through which the auricula-temporalis nerves and supra-temporal arteries pass, the appliance comprising:

(a) a pair of occlusal posterior pads made of triple composite material with a base having a top layer of impressionable material, an intermediate layer of hard material and a somewhat impressionable bottom layer; and (b) a continuous vertical arch open anteriorly and posteriorly, extending from the occlusal posterior pads and adapted to expand and contract to be molded to the palate and adapted to lie along the palate out of the way of the tongue extending directly across to and connecting the posterior pads together within the mouth.

2. The dental appliance of claim 1, further comprising a tunnel beneath the arch and defined by the arch and the occlusal posterior pads, the tunnel being completely open anteriorly and posteriorly thereby allowing unobstructed movement of the tongue anteriorly and posteriorly.

3. The dental appliance of claim 1, further comprising a stiffener embedded within the arch.

4. The dental appliance of claim 3, wherein the stiffener is expandable and contractible, thereby following the arch as it is molded to the palate.

5. The dental appliance of claim 3, wherein the stiffener is serpentine, further comprising a series of loops winding back and forth across the arch.

6. The dental appliance of claim 3, wherein the stiffener is constructed of said hard material and is continues with said intermediate layer.

7. The dental appliance of claim 1, further comprising a plurality of protrusions adapted to engage the central fossae of the posterior teeth of the upper jaw, thereby positioning the occlusal pads in engagement with the posterior teeth, pre-molars and molars.

8. The dental appliance of claim 7, wherein the protrusions are constructed of said somewhat impressionable material, extending from said bottom layer through said intermediate layer and said top layer.

9. The dental appliance of claim 1, wherein said bottom layer is wedge-shaped, being thicker posteriorly and thinner anteriorly, thereby forcing the condyle of the jaw to move downwardly and forwardly away from the auricula-temporalis nerves and supra-temporal arteries.

10. The dental appliance of claim 9, wherein said impressionable layer comprises about 50% by weight of a polycaprolactone polymer and about 50% by weight of ethylene vinyl acetate.

11. The dental appliance of claim 1, wherein said impressionable layer is softenable by heat.

12. The dental appliance of claim 1, wherein said impressionable layer is soft while in the dark and hardens when exposed to light.

13. The dental appliance of claim 1, wherein said intermediate layer comprises a thermoplastic.

14. The dental appliance of claim 1, wherein said intermediate layer comprises a thermoplastic rubber.

15. The dental appliance of claim 14, wherein said bottom layer comprises about a 50% by weight of Kraton and about a 50% by weight of ethylene vinyl acetate.

16. The dental appliance of claim 15, further comprising a straw adapted for sucking cold water into the mouth to cool the impressionable material after fitting.

17. The dental appliance of claim 16, wherein the straw is formed within the handle.

18. The dental appliance of claim 16, wherein the straw is attached to the handle.

19. The dental appliance of claim 1, wherein said bottom layer comprises a thermoplastic elastomer.

20. The dental appliance of claim 1, further comprising a removable handle adapted for dipping the appliance into warm water to soften the impressionable material and inserting the appliance into the mouth for fitting.

* * * * *